United States Patent [19]

Baskeyfield et al.

[11] 4,182,916
[45] Jan. 8, 1980

[54] METHOD FOR THE PRODUCTION OF 6-HYDROXY-1,2,3,4-TETRAHYDRONAPHTHALENE

[75] Inventors: Lewis J. Baskeyfield, Stoke-on-Trent; John D. Bell, Keyworth; John Townend, Crewe; Simon D. A. Pollock, Loughborough, all of England

[73] Assignee: Fisons Limited, London, England

[21] Appl. No.: 864,256

[22] Filed: Dec. 27, 1977

[30] Foreign Application Priority Data

Jan. 7, 1977 [GB] United Kingdom ................ 496/77

[51] Int. Cl.² .............................................. C07C 39/12
[52] U.S. Cl. ...................................... 568/734; 568/735
[58] Field of Search ................ 568/740, 734, 758, 735

[56] References Cited

U.S. PATENT DOCUMENTS

| | | | |
|---|---|---|---|
| 3,340,311 | 9/1967 | Chitwood et al. | 568/740 |
| 3,356,743 | 12/1967 | Freure | 568/740 |
| 3,402,210 | 9/1968 | Hiser | 568/740 |
| 3,935,282 | 1/1976 | Kudo | 568/740 |

FOREIGN PATENT DOCUMENTS 2150753 4/1972 Fed. Rep. of Germany ........... 568/758
2153329 4/1972 Fed. Rep. of Germany ........... 568/758

*Primary Examiner*—Werren B. Lone
*Attorney, Agent, or Firm*—Merriam, Marshall & Bicknell

[57] ABSTRACT

There is described a process for the production of 6-hydroxy-1,2,3,4-tetrahydronaphthalene of formula I,

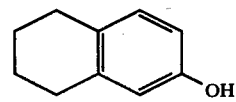

I which comprises treatment of beta naphthol with an absorbant, removal of the absorbant and selective hydrogenation of the resulting beta naphthol, preferably in a solvent which is inert under the reaction conditions. There is also described a process for the production of a compound of formula I using a rhodium catalyst.

15 Claims, No Drawings

METHOD FOR THE PRODUCTION OF 6-HYDROXY-1,2,3,4-TETRAHYDRONAPHTHALENE

This invention relates to a new process.

According to the invention there is provided a process for the production of 6-hydroxy-1,2,3,4-tetrahydronaphthalene of formula I,

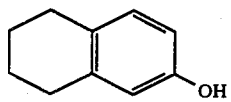

which comprises treatment of beta naphthol with an absorbant selected from silica, aluminia and charcoal, removal of the absorbant and selective hydrogenation of the resulting beta naphthol. The hydrogenation is preferably carried out in a solvent which is inert under the reaction conditions.

The treatment of the beta naphthol with the absorbant is preferably carried out at an elevated temperature, e.g. of from about 40° C. to the reflux temperature of the beta naphthol. We prefer the absorbant to be charcoal, and we prefer the charcoal to have some or all of the following characteristics:

surface area 1,000–1,500 M²/g,
bulk density of 0.47 to 0.51 g/cc,
particle size of 5 to 20 microns,
an ash content of 3 to 4% by weight,
an aqueous extract pH of 9.5 to 10.5,
the majority of the pores with radii in the range 10–15 Angstrom units,
and in particular to be charcoal derived from coconut shell.

We prefer to use from 5 to 50%, more preferably from 5 to 20% and most preferably from 5 to 15% by weight of absorbant based on the weight of beta naphthol used. The absorbant and the beta naphthol are preferably contacted for from 1 to 4, and preferably for about 2 hours. The absorbant may be separated from the beta naphthol by conventional techniques, e.g. filtration. Surprisingly we have found that it is necessary to remove the absorbant from the beta naphthol to obtain satisfactory improvements in the process. The treatment with the absorbant enables the process to be operated economically at higher concentrations of beta naphthol in the solvent and/or with lower catalyst loading.

The hydrogenation may be carried out under acidic or preferably under neutral conditions. Acidic conditions may be provided by the addition of, for example hydrochloric, hydrobromic, sulphuric or phosphoric acid. The optimum proportion of acid used and the effect of the presence of water on the reaction may be determined by routine experimentation.

While it is desirable that the reaction conditions and the catalyst used be such as to minimise the production of unwanted bi-products, a certain level of impurities in the reaction product is acceptable. Such impurities can in general be removed from the reaction product by, for example solvent extraction (preferably of a salt, such as the sodium salt, of the reaction product), distillation (e.g. high vacuum fractional distillation) or crystallisation, e.g. from a mixture of benzene and hexane. It is, however, relatively difficult to remove starting material from the product and we prefer processes giving low levels of starting material in the product.

The hydrogenation may be carried out at a temperature of from about 40° to 140° preferably 40° to 120°, and most preferably from 80° to 100° C.

The hydrogenation may be carried out in a solvent which is inert under the reaction conditions, e.g. a lower C 1 to 6 alkanol such as propanol, butanol or preferably ethanol or methanol; a lower alkyl ketone such as acetone or methyl ethyl ketone; an organic acid, e.g. a lower alkanoic acid such as acetic acid; or an ester, e.g. a lower alkyl ester such as ethyl acetate or propyl acetate. The solvent is preferably water miscible. A mixture of solvents may also be used. The concentration of the beta naphthol in the solvent is preferably from about 5 to 30%, more preferably 5 to 25%, and most preferably about 20% w/v.

The proportion of the metal catalyst to the beta-naphthol is preferably in the range 0.05 to 10:100, e.g. 0.5:100 by weight. When a rhodium catalyst is used we prefer to use a proportion of catalyst to beta naphthol in the range 0.05 to 5:100 and preferably 0.2 to 0.5:100 by weight. The catalyst may if desired be added to the reaction mixture in portions as the reaction progresses.

The reaction is preferably carried out for the minimum time necessary to convert more than 99%, and preferably all of the starting material to the desired product. However the reaction is preferably not continued for so long that a substantial proportion of the desired product is further reduced to unwanted bi-products.

The reaction may be carried out at pressures of from 0 to 60, preferably from 10 to 40, and most preferably from 20 to 30, atmospheres gauge.

It is desirable that the reaction be carried out as rapidly as possible and we therefore prefer the reaction mixture to be vigourously agitated, e.g. by shaking or more preferably by stirring. When the reaction is performed on a batch basis we prefer the reaction to be carried out for less than 4 hours.

The catalyst may be a conventional hydrogenation catalyst, e.g. a precious metal catalyst. The catalyst, and the conditions under which it is used, are preferably such as to produce the optimum yield of the desired product and to avoid, in so far as is possible, the production of undesirable bi-products, e.g. decalol, decalone and 2-hydroxy-1,2,3,4-tetrahydronaphthalene. It is also desirable that when an expensive catalyst, e.g. a precious metal catalyst, is used that the most economic proportion of catalyst is used.

The catalyst may be supported on a suitable support, e.g. carbon, alumina, barium sulphate or calcium carbonate.

In particular we have found that a rhodium catalyst is suitable, but other catalysts, and the optimum conditions under which they can be used, can be found by routine experimentation. Catalysts which may be mentioned include 10%—Palladium on Carbon
5%—Palladium on Carbon. Unreduced
3%—Palladium on Carbon. 50% Moisture
5%—Palladium on Carbon. 50% Moisture. Sulfided
5%—Palladium on Carbon
5%—Palladium on Alumina
5%—Palladium on Barium Sulfate
5%—Palladium on Calcium Carbonate
5%—Platinum on Carbon
5%—Platinum on Carbon. 50% Moisture. Sulfided 1%—Platinum on Carbon. 50% Moisture
5%—Platinum on Alumina
3%—Rhodium on Carbon
5%—Rhodium on Carbon
5%—Ruthenium on Alumina
5%—Ruthenium on Carbon
0.5%—Palladium on Granular Carbon
0.5%—Palladium on Alumina Pellets
0.1%—Palladium on Alumina Pellets
0.5%—Platinum on Alumina Pellets
0.5%—Ruthenium on Alumina Pellets
Platinum oxide.

We prefer catalysts containing 3% or more of precious metal, and in particular we prefer 5% rhodium on carbon. The catalyst may if desired contain water.

According to the invention there is also provided a process for the production of a compound of formula I which comprises selective hydrogenation of beta-naphthol in a solvent which is inert under the reaction conditions and using a rhodium catalyst.

The hydrogenation is preferably carried out under the conditions specified above. The use of a rhodium catalyst enables the yields of the desired product to be maximised and the quantities of unwanted bi-products to be minimised and to be carried out at relatively low pressures.

The hydrogenation may be carried out in apparatus conventionally used for catalytic hydrogenations, e.g. comprising a stirred reactor, but we prefer to carry out the hydrogenation under neutral conditions and in an apparatus comprising a self priming mixing jet. In such an apparatus the major part of the reaction takes place in the mixing jet and, because of the high shear forces prevailing, a higher rate of reaction occurs than in conventional stirred reactors. The reaction mixture is continuously circulated through the mixing jet. The apparatus is also provided with heat exchange units to ensure control of the temperature of the reaction mixture. One form of suitable apparatus is available from Buss AG Basel, Switzerland.

The invention is illustrated, but in no way limited by the following Example in which the temperatures are in degrees centigrade.

EXAMPLE

6-Hydroxy-1,2,3,4-tetrahydronaphthalene

2-Hydroxynaphthalene (60 g) was added to a stirred suspension of carbon (6 g) and methanol (300 ml) and the mixture heated under gentle reflux for 2 hours. After cooling to ambient temperature the carbon was removed by filtration. 5% Rhodium on charcoal catalyst (3g) was added to the resulting solution. The mixture was stirred with hydrogen at 25–30 atmospheres at 85°–90°. Reaction was complete after 1½ hours. The catalyst was removed by filtration, and the solvent removed under reduced pressure. The crude solid product was dissolved in dilute sodium hydroxide solution (360 ml) and washed with toluene (3×120 ml portions). Concentrated hydrochloric acid (80 ml) was then added and the crude product precipitated from the solution. The product was filtered off and dried. Dry weight=43.2 g m.p. 58°–62°.

We claim:

1. A process for the production of 6-hydroxy-1,2,3,4-tetrahydronaphthalene of formula I,

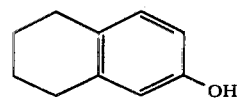

which comprises treating beta naphthol with an absorbant selected from silica, alumina and charcoal, at a temperature in the range from 40° C. to the reflux temperature of beta naphthol, removing the absorbant and selectively hydrogenating the resulting beta naphthol with hydrogen at a pressure of 0–60 atmospheres gauge and a temperature of 40°–140° C., in the presence of a hydrogenation catalyst comprising rhodium, palladium, platinum or ruthenium, the proportion of said catalyst to said beta naphthol being in the range from 0.05:100 to 10:100 by weight.

2. A process according to claim 1, wherein the absorbant is charcoal.

3. A process according to claim 2, wherein the charcoal has a surface area of 1,000 to 1,500 $M^2/g$, a bulk density of 0.47 to 0.51 g/cc, a particle size of 5 to 20 microns, an ash content of 3 to 4% by weight, an aqueous extract pH of 9.5 to 10.5, and the majority of pores have radii in the range 10–15 Angstrom units.

4. A process according to claim 2, wherein the charcoal is derived from coconut shell.

5. A process according to claim 1, wherein from 5 to 50% by weight of absorbant is used, based on the weight of beta naphthol.

6. A process according to claim 1, wherein the absorbant and the beta naphthol are contacted for from 1 to 4 hours.

7. A process for the production of a compound of formula I, as defined in claim 1, which comprises selective hydrogenation of beta-naphthol in a solvent which is inert under the reaction conditions and using a rhodium catalyst.

8. A process according to claim 1, wherein the hydrogenation is carried out under neutral conditions.

9. A process according to claim 1, wherein the hydrogenation is carried out at a temperature of from 40° to 140° C.

10. A process according to claim 1, wherein the hydrogenation is carried out in a lower alkanol, a lower alkyl ketone, an organic acid or an ester as solvent.

11. A process according to claim 10, wherein the concentration of the beta naphthol in the solvent is from 5 to 30% w/v.

12. A process according to claim 1, wherein the catalyst is added to the reaction mixture in portions as the reaction progresses.

13. A process according to claim 1, wherein the hydrogenation is carried out at a pressure of from 0 to 60 atmospheres gauge.

14. A process according to claim 1, wherein the catalyst is a rhodium catalyst supported on carbon.

15. A process according to claim 14 wherein the catalyst is 5% rhodium on carbon.

* * * * *

UNITED STATES PATENT AND TRADEMARK OFFICE
CERTIFICATE OF CORRECTION

PATENT NO. : 4,182,916

DATED : January 8, 1980

INVENTOR(S) : LEWIS J. BASKEYFIELD ET AL.

It is certified that error appears in the above-identified patent and that said Letters Patent are hereby corrected as shown below:

Col. 3, line 52, "53" should be

-- 5% --

Signed and Sealed this

Twenty-second Day of April 1980

[SEAL]

Attest:

SIDNEY A. DIAMOND

Attesting Officer     Commissioner of Patents and Trademarks